United States Patent [19]

Bach

[11] Patent Number: 5,894,130

[45] Date of Patent: Apr. 13, 1999

[54] ULTRAVIOLET STERILIZATION UNIT

[75] Inventor: Stanley W. Bach, Moreland Hills, Ohio

[73] Assignee: Aquatron, Inc., Solon, Ohio

[21] Appl. No.: 08/907,536

[22] Filed: Aug. 8, 1997

[51] Int. Cl.$^6$ ................................................. A61L 2/10
[52] U.S. Cl. .................. 250/436; 250/504 R; 422/24; 422/121
[58] Field of Search .................. 250/436, 455.11, 250/504 R; 422/24, 121

[56] References Cited

U.S. PATENT DOCUMENTS

| | | | |
|---|---|---|---|
| 3,551,091 | 12/1970 | Veloz | 250/436 |
| 4,931,654 | 6/1990 | Horng | 250/436 |
| 5,523,057 | 6/1996 | Mazzilli | 250/436 |

OTHER PUBLICATIONS

"Air Irradiation in Heating and Air–Conditioning Ducts", pp.5–9 (untitled, undated publication).

"Sterilamp Germicidal Ultraviolet Tubes", *Westinghouse*, pp. 11, 8, 13, 5 and 3, (undated publication).

"What are *American Ultraviolet* sterile conditioners?", 4 pp., untitled, undated publication.

*Primary Examiner*—Jack I. Berman
*Attorney, Agent, or Firm*—Fay, Sharpe, Beall, Fagan, Minnich & McKee

[57] ABSTRACT

An ultraviolet sterilization unit having a housing attached to an air heating and cooling system. The housing including two apertures into which lamp cartridges are inserted. The lamp cartridges carrying ultraviolet lamps operating in a frequency capable of sterilizing air within the system. The cartridges are configured to automatically de-energize the lamps when a lamp cartridge is removed from the housing. When the sterilization unit is a multiple lamp system, when one of the lamp cartridges is removed all lamps are de-energized. The de-energizing of the lamps occurring before a user will view the lamp.

20 Claims, 10 Drawing Sheets

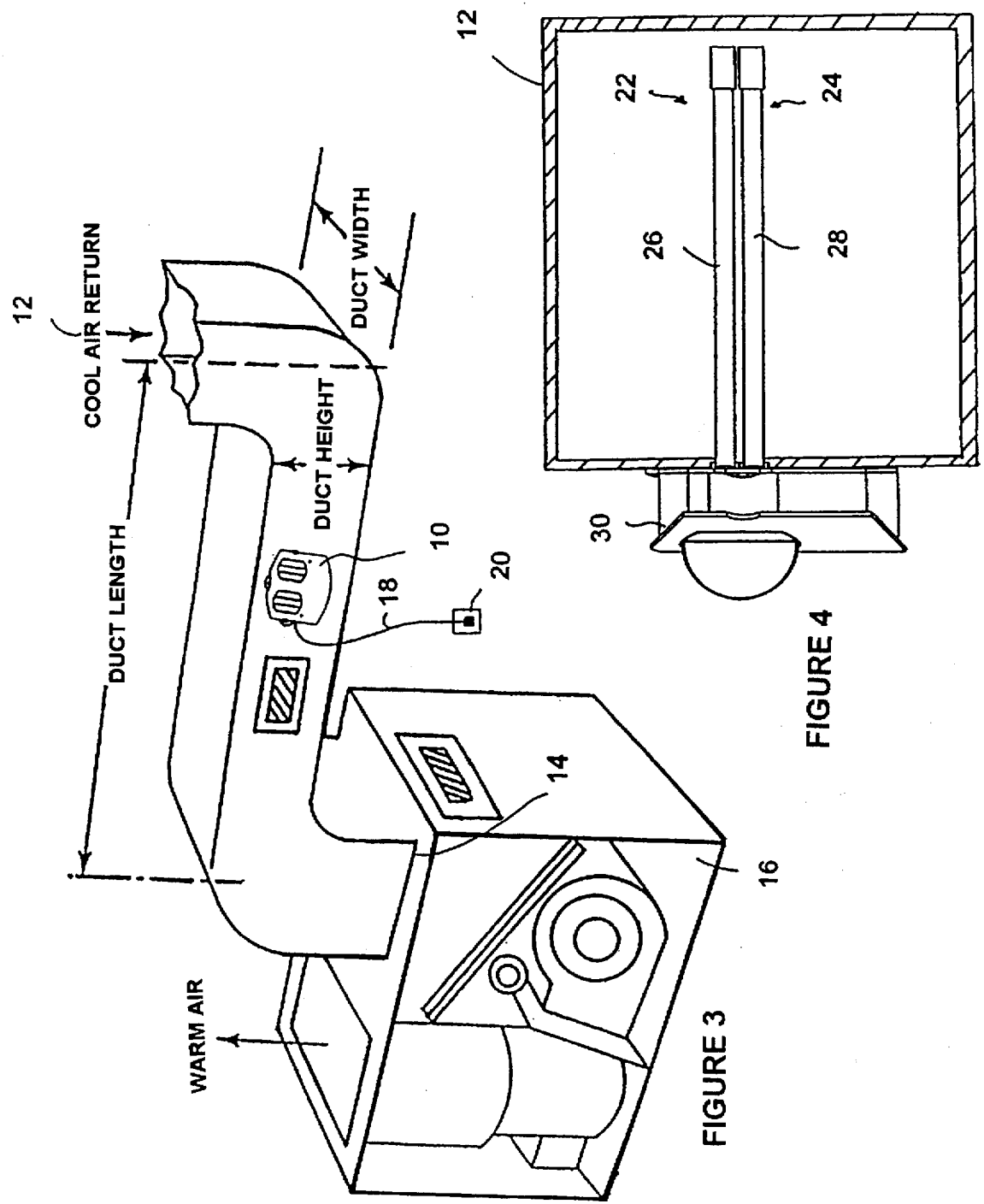

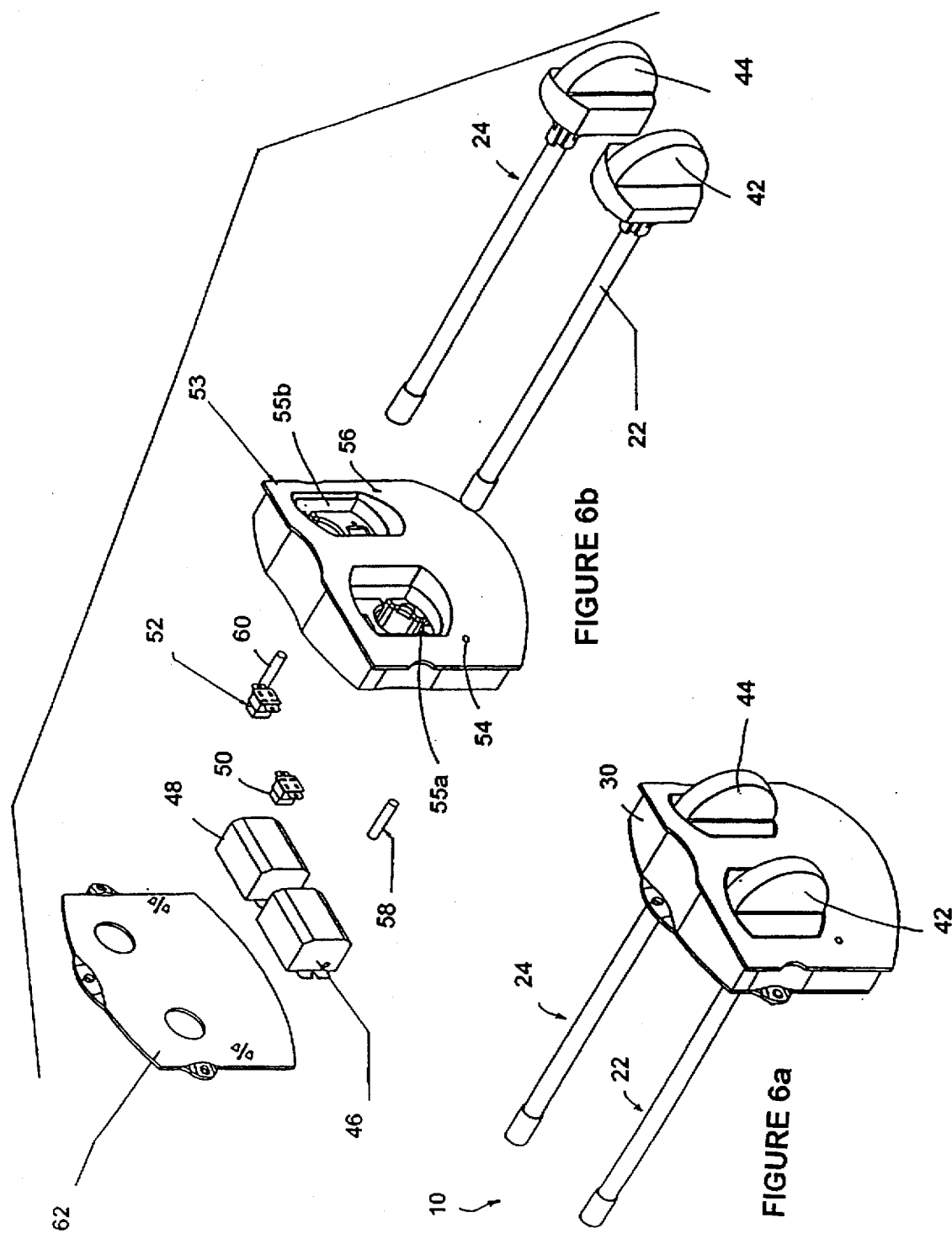

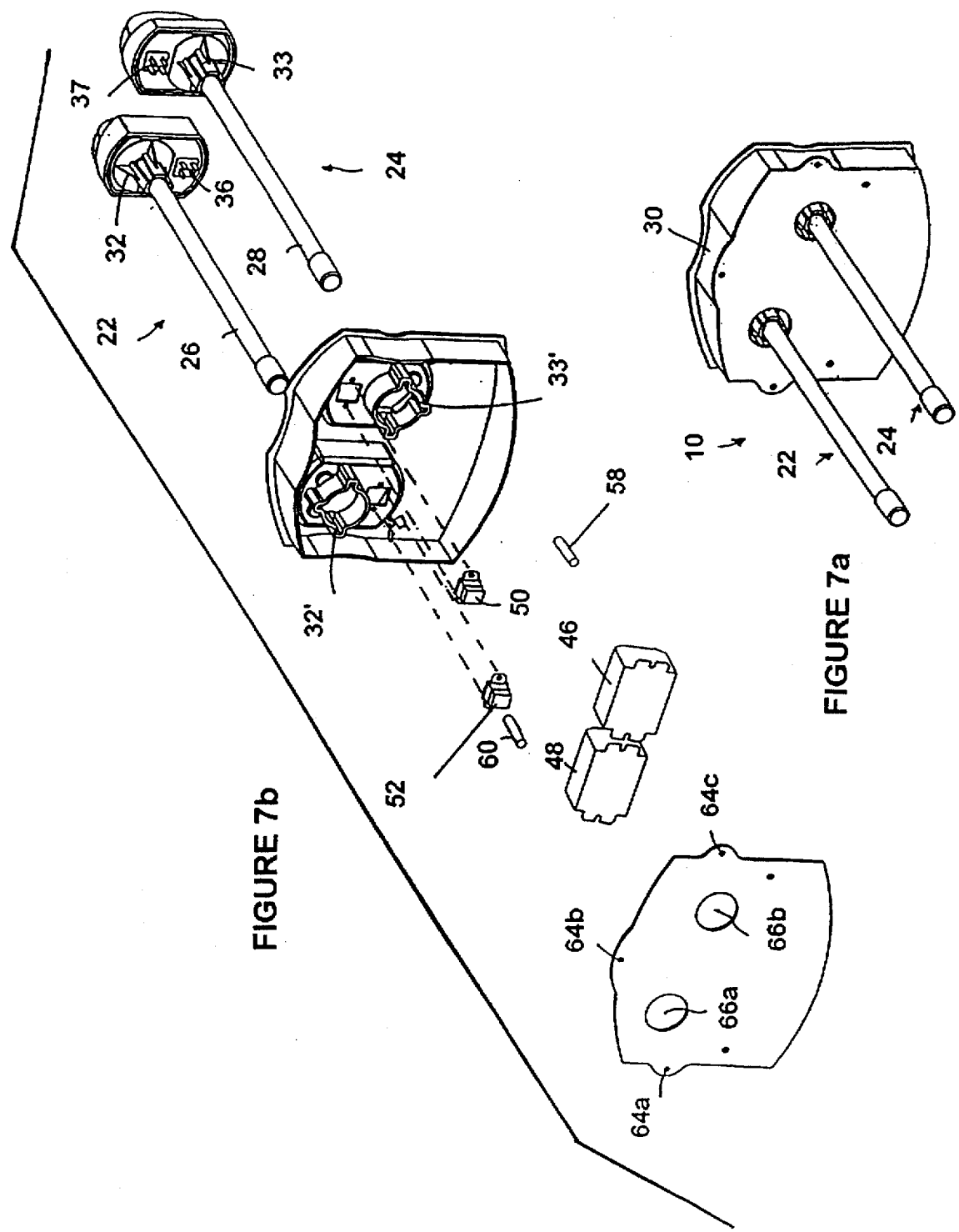

1

ULTRAVIOLET STERILIZATION UNIT

BACKGROUND OF THE INVENTION

This invention pertains to the art of ultraviolet germicidal lamps used for air sterilization.

The invention is applicable to compact ultraviolet germicidal sterilization units which are inserted within the air ducts of forced air heating and cooling systems, and will be described with particular reference thereto. It will be appreciated, however, that the invention has broader applications and may be advantageously employed in other environments and applications that benefit from the sterilization of recirculated air.

Ultraviolet energy which can be grouped into three wavelength categories, "long," "middle," and "short" wave ultraviolet, has been shown to be beneficial for a variety of uses. All of ultraviolet wavelengths are shorter than visible light waves and, therefore, are invisible to the human eye.

It has been further shown that ultraviolet wavelengths in the short wave category, and in particular in the region of 253.7 nm, are useful in the destruction of bacteria and other micro-organisms in the air or on exposed surfaces. Micro-organisms which are invisible to the unaided eye, include bacteria, mold spores, yeast and viruses. Each of these are microbes, but different from each other. Microbes are living cells approximately 1/25,000 of an inch in length which reproduce by one cell dividing every twenty minutes or faster. This is a continuous cycle and, if left unchecked, from one bacteria there would be several billion bacteria in less than twelve hours. Indoor air may contain countless bacteria and mold spores and/or viruses, which are the source of spoilage of perishable products and the cause of disease in humans and animals. Germicidal rays emitted by ultraviolet lamps in the short wavelengths in the range of 253.7 nm travel through the air and destroy micro-organisms which are in the path of the rays.

In order for the ultraviolet rays to kill bacteria, etc., the rays must directly strike the micro-organisms. Thus, micro-organisms floating in the air may easily be reached by the ultraviolet rays and, therefore, are readily destroyed. Exposure to ultraviolet rays necessary to kill bacteria, etc. is the product of time and intensity. High intensity for a short period of time, or low intensity for a long period are fundamentally equal in lethal action on bacteria (disregarding the life cycle of the bacteria).

It has been found that the characteristics of germicidal ultraviolet, i.e. those rays in the short wavelength region of 253.7 nm, are useful in air heating and cooling systems to make the air passing through system ducts equivalent, as much as possible, to outdoor air in freedom from live bacteria, etc.

In the average installation, a 90% kill of air borne bacteria, equivalent to most outside air, is recommended. Where a maximum sterilization is imperative, as in hospitals and pharmaceutical laboratories, the highest bacterial reduction possible is desirable—at least 98%. Such conditions can be obtained by increasing the number of lamps in the air conditioning system.

Since the effectiveness of their radiation increases with time of exposure, ultraviolet (germicidal) are known to be installed in the part of the heating and cooling system where the air velocity is the lowest. It has been determined that placement after the filters, if at all possible, is optimal.

A specific example of existing ultraviolet sterilization equipment inserted within forced air heating and cooling system A is illustrated in FIG. 1. Sterilization equipment B is located at an intake end of cool air return duct D, and sterilization equipment C is located in a centralized area of cool air return duct D. A preferred location for placement of sterilization equipment C is within the cool air return D. While ultraviolet lamps can be placed on the warm air side of the system, this tends to decrease the life of the ultraviolet lamps. As can be seen more closely in FIGS. 2a–2c, such lamps are presently arranged in a variety of configurations, including FIG. 2a which is a lamp holder E with one lamp F, FIG. 2b a lamp holder G with two lamps H, I as well as FIG. 2c which is a sixteen lamp grid J arrangement four feet square by eighteen inches deep. Thus, existing units may be used in a small installations such as found in homes, as well as in larger industrial type heating/air conditioning systems found in commercial buildings.

A drawback known to exist in using germicidal ultraviolet lamps for sterilizing recirculating air is that the rays from ultraviolet lamps are harmful to the eyes and skin of humans and animals.

For this reason, in personal protection applications, that is, the use of the lamps for room irradiation in homes, schools, offices, etc., indirect fixtures are placed on the wall or suspended from the ceiling above eye level. Only the upper air is irradiated and the people occupying the room should receive no direct radiation. It is also known that plant life may be damaged by direct or reflected germicidal ultraviolet rays and transient dyes and colors will fade from exposure to ultraviolet rays.

When sterilization equipment such as B and C are within the forced air heating and cooling system A, there is no concern as to harm to humans, animals, plants, etc. However, over time the lamps degrade and need to be replaced. Also, it is important that functioning lamps be kept on a maintenance schedule which includes cleaning and inspection. Dust in the air within air ducts tend to cover the lamps, thereby degrading their usefulness by limiting the intensity and amount of ultraviolet rays emitted. Cleaning, inspection and replacement of lamps require complete removal of equipment B and C from heating and cooling system A.

A concern with removal of such sterilization equipment is the possibility of harm being caused due to the lamps being removed while they are energized. Manufacturers of these units address the issue of safety by requiring large "Caution" notices and other warnings near the lamp fixtures instructing a person to ensure that they de-energize the lamps prior to working near the installation. The commonly suggested warning is that no one should look directly at a lighted lamp, or work near a lighted lamp without adequate eye protection. It is further suggested that tube and reflector cleaning and tube replacement should be entrusted only to personnel who will observe the strict precaution of never exposing the face and eyes to a lighted tube while they are working on it or on the reflector. It is noted that reflectors are often used to direct the rays of the lamps in installations.

In larger units such as the sixteen lamp configuration J shown in FIG. 2c, it is possible to provide an access door for periodic checking and cleaning of the lamps in a chamber or air duct in which the lamps are mounted. As a safety measure, some installations configure the door so it is locked with an electrical circuit such that the lamps are turned off automatically when the door is open. Further, a window of ordinary glass, which filters out the ultraviolet, is provided to allow safe observation of the lamps.

Thus, as illustrated in FIGS. 1 and 2, for small size installations, such as household use, etc. the manner of ensuring that harmful rays are not viewed by a user replacing or cleaning ultraviolet lamps, is the use of a "caution" notice. However, in many instances such caution notices are either ignored, accidentally removed, or otherwise not effective, resulting in a user looking directly at an energized lamp, without adequate eye protection.

Further, while there is a certain degree of control in large industrial settings, such as ensuring automatic turn off of the lamps when a door is open, these turn offs are not implemented in the smaller sized settings. Particularly, in the smaller installations no access door provided, due in part to size constraints. In view of the foregoing, if there is an increase in the number of sterilization units used in residential or smaller settings, there will likely be a corresponding increase in the number of users forgetting or ignoring instructions to de-energize the lamps and/or otherwise not following the proper precautions resulting in an increase in injuries.

Thus, there has not been a wide use of ultraviolet sterilization equipment in residential or smaller installations where de-energizing of the lamps is not ensured. This is in part due to manufacturers' concerns of being liable for injuries sustained by a person misusing the sterilization equipment. The above factors result in an undesirable situation where bacteria and other micro-organisms, which would otherwise be destroyed, through application of ultraviolet rays are recirculated through an air heating and cooling systems thereby increasing the spread of viruses, bacteria, etc. in these settings.

Therefore, it has been deemed desirable to develop an ultraviolet sterilization unit for use in forced air heating and cooling systems which ensures the turning off/de-energizing of an ultraviolet lamp prior to exposing the lamp to the view of a user. Further, the ultraviolet sterilization unit should be compact and easy to insert within the air heating and cooling ducts thereby encouraging those with limited mechanical capabilities to install the unit. Still further, the ultraviolet sterilization unit should be configured for use with multiple lamps and should ensure the turning off of all lamps in the multiple lamp unit when any one of the lamps is removed and/or exposed to human view.

SUMMARY OF THE INVENTION

The present invention contemplates a new and improved ultraviolet sterilization unit that overcomes all of the above noted problems and others, and full proofs the turning off of all lamps within the unit when any one lamp is removed and/or exposed to human view.

According to a more limited aspect of the invention, the ultraviolet sterilization unit is made to be easily attached and inserted into an air heating and cooling system, causing minimal disruption of the air heating and cooling system.

According to yet another aspect of the invention, ultraviolet lamps in a multiple lamp unit are offset from each other thereby increasing the area irradiated by ultraviolet rays.

According to still a further aspect of the invention, the ultraviolet sterilization unit is configured such that it may be rotated 90° to locate lamps at right angles to the air flow thereby increasing the air flow irradiated by the ultraviolet rays.

A principal advantage of the invention is provision of an ultraviolet sterilization unit that eliminates a high percentage of air borne micro-organisms in recirculated air and which ensures safe removal of an ultraviolet lamp of the unit by automatically de-energizing all lamps within a unit upon removal of any one lamp.

Another advantage of the invention resides in the ease with which the unit may be attached and inserted into an existing air heating and cooling system.

Still other advantages and benefits of the invention will become apparent to those skilled in the art upon a reading and understanding of the detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 3 is an air heating and cooling system incorporating an ultraviolet sterilization unit according to the teachings of the present invention;

FIG. 4 is an expanded view of a section of FIG. 3 providing a side view of the ultraviolet sterilization unit of the present invention;

FIG. 5a depicts a single lamp cartridge including an ultraviolet lamp, according to the teachings of the present invention;

FIG. 5b is an exploded view of FIG. 5a;

FIG. 6a depicts an ultraviolet sterilization unit of the present invention implemented in a two lamp configuration;

FIG. 6b is an exploded view of FIG. 6a;

FIG. 7a depicts an alternative view of the ultraviolet sterilization unit of FIG. 6a;

FIG. 7b is an exploded view of FIG. 7a;

DETAILED DESCRIPTION OF THE PREFERRED EMBODIMENT

Figure 1:
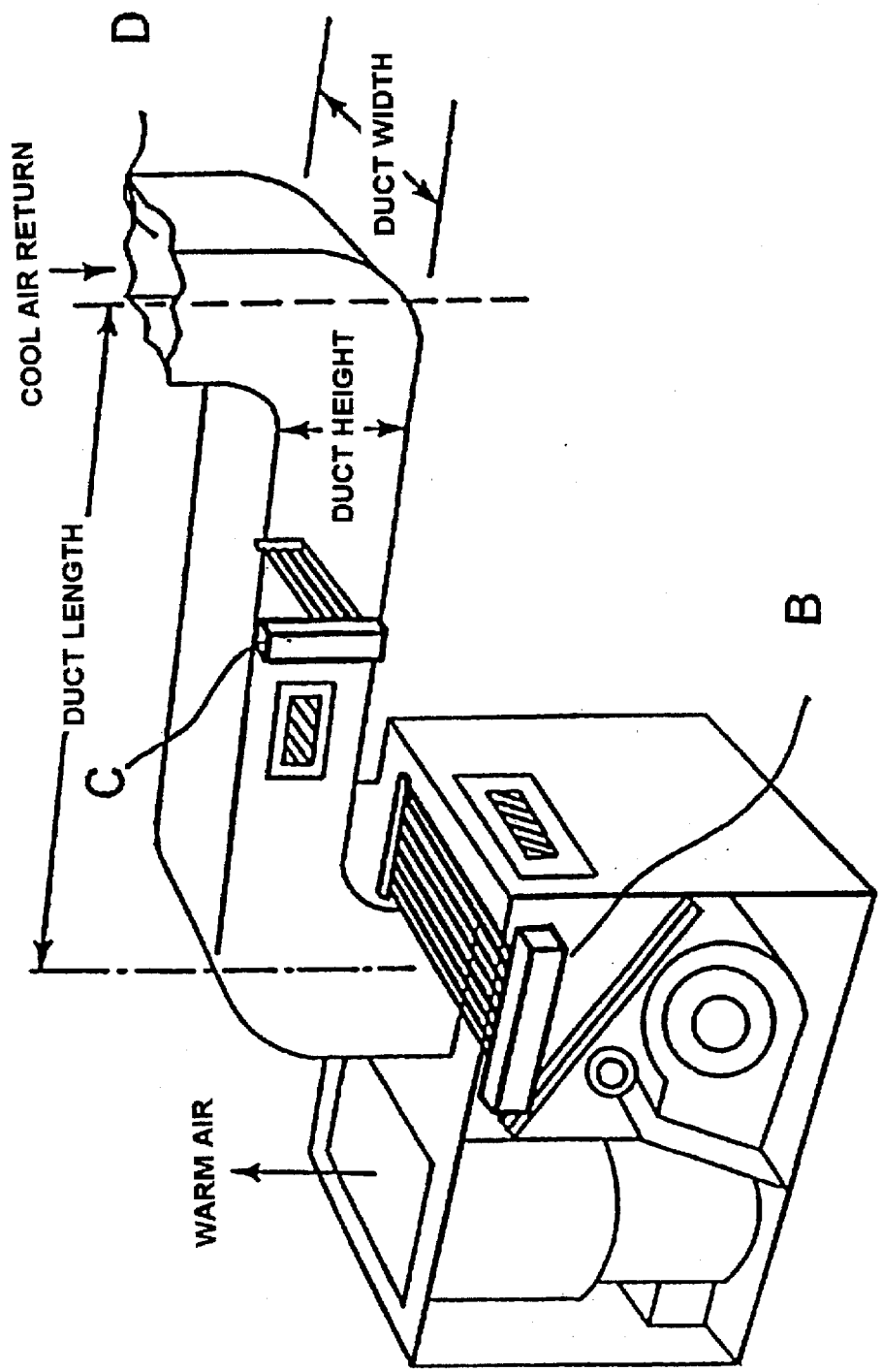
FIG. 1 is an air heating and cooling system with existing sterilization equipment.
Figure 2A:
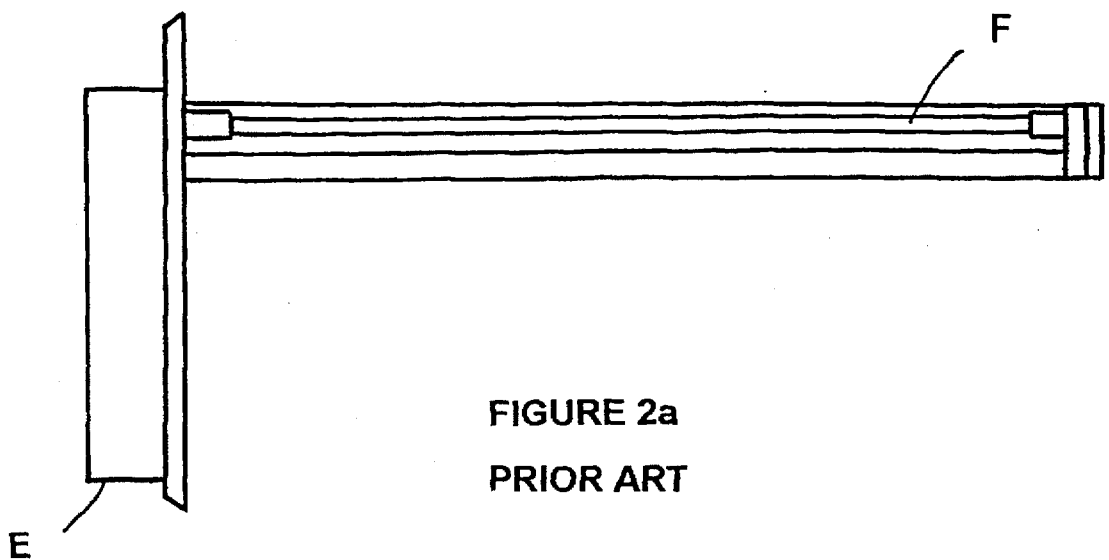
FIGS. 2a–2c are a variety of existing ultraviolet sterilization lamp configuration.
Figure 2B:
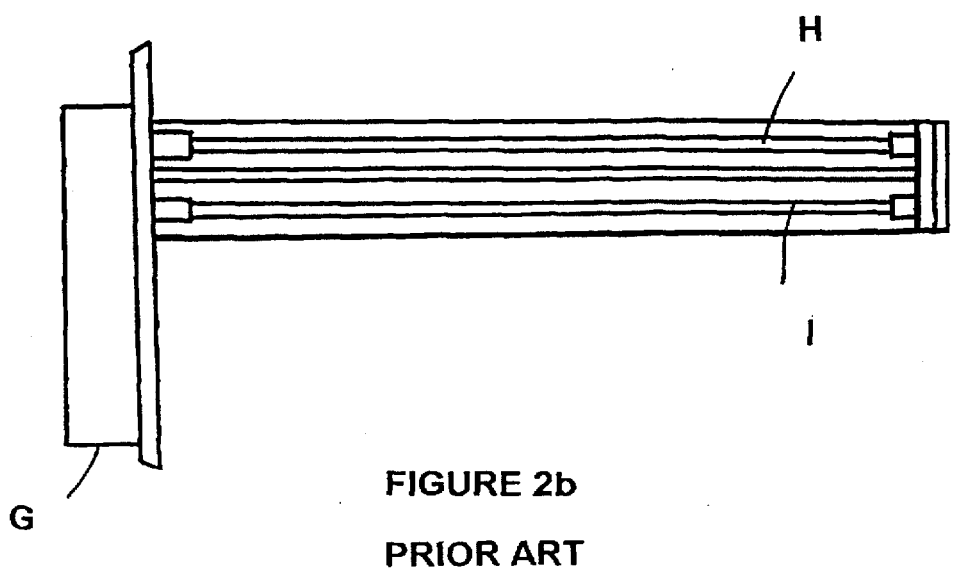
Figure 2C:
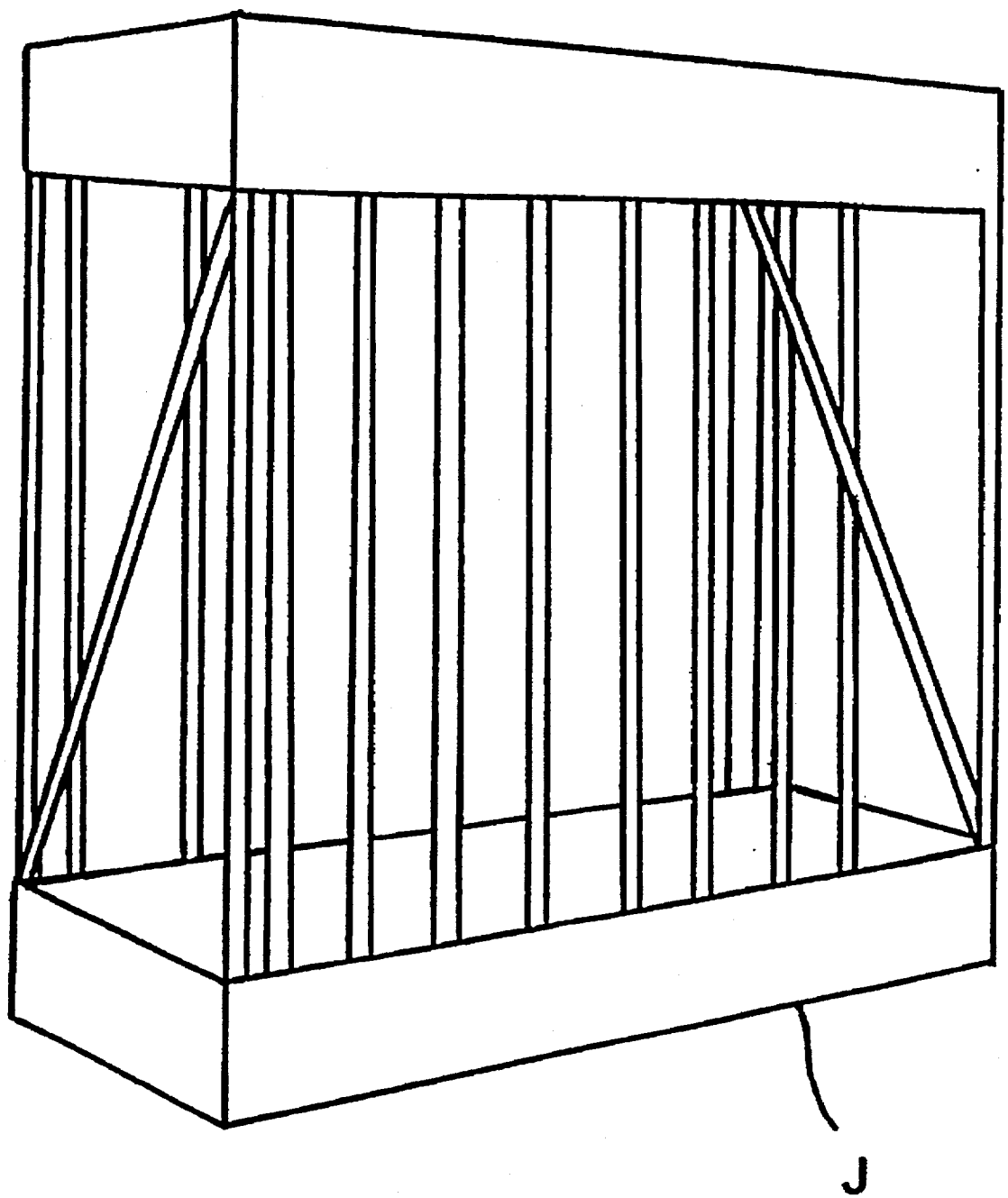

Referring now to the drawings wherein the showings are for purposes of illustrating a preferred embodiment of the invention only and not for purposes of limiting same, FIGS. 1 and 2a–2b illustrate the previous discussed ultraviolet sterilization equipment arranged to be included within a forced air heating and cooling system.

FIG. 3 depicts a forced air heating and cooling system A such as that in FIG. 1. However, in this embodiment, ultraviolet sterilization unit 10, configured according to the teachings of the present invention, has been inserted within the cool air return 12 of air heating and cooling system A. Although not shown, ultraviolet sterilization unit 10 may also be placed in other locations within system A including the connection 14 between cool air return 12 and heating/cooling unit 16. Ultraviolet sterilization unit 10 is provided with power through power cord 18 which is connected to a normal household outlet 20 and sterilization unit 10. It is to be appreciated that other known sources of power may also be used.

FIG. 4 is a side view of ultraviolet sterilization unit 10 inserted through, a cut-away section of the duct work of cool air return 12. Ultraviolet sterilization unit 10 of FIG. 4 includes two ultraviolet lamp cartridges 22, 24 holding ultraviolet lamps 26 and 28 and carried within main housing 30.

Figures 5A, 5B:
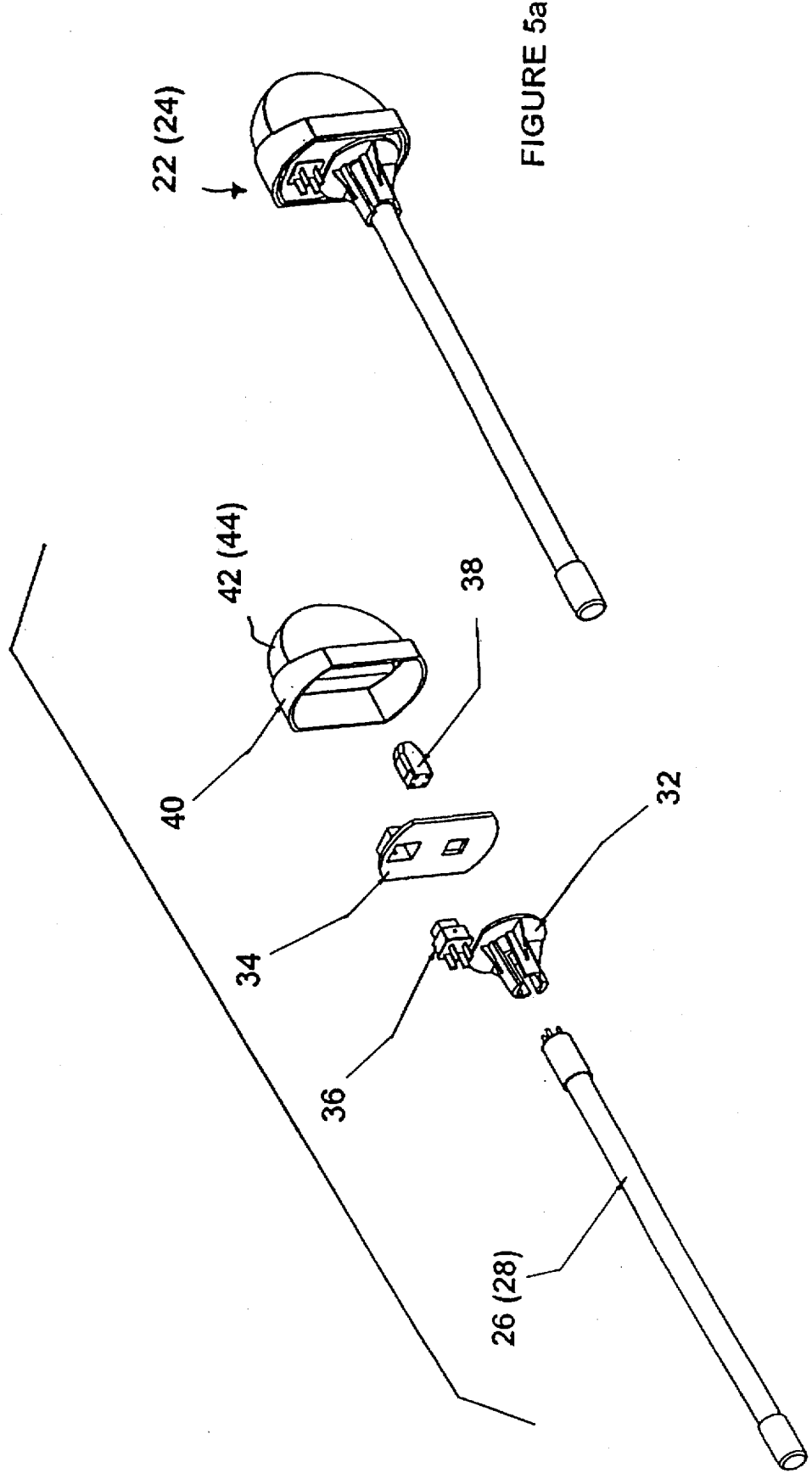

Turning attention to FIGS. 5a and 5b, lamp cartridges 22 and 24 will be described in greater detail. It is to be appreciated the following discussion is equally applicable for both cartridges 22 and 24, with FIG. 5a depicting an assembled lamp cartridge 22 (24). FIG. 5b is an exploded view of FIG. 5a, where ultraviolet (germicidal) lamp 26 (28) is aligned for insertion within lamp holder 32. Lamp holder 32 may be of different configurations, but includes a manner of gripping ultraviolet lamp 26 (28) in a secure fashion.

It is to be appreciated that a variety of different ultraviolet lamps may be used in sterilization unit 10, including a single ended germicidal lamp such as those sold under the STE-RILAMP brand name (STERILAMP is a trademark of Westinghouse Corporation). Particular lamps of this type include slimline lamps (G36T6L and G105½H) which are designed for sterilization applications. Their high ultraviolet output permits the efficient radiation of rapidly moving air. At the 300 to 400 milli-amp current loading the moderate cooling of the bulb system increases, rather than decreases the ultraviolet output. These lamps are effective germicidal lamps for residential-sized forced air heating and cooling systems.

Figure 8:
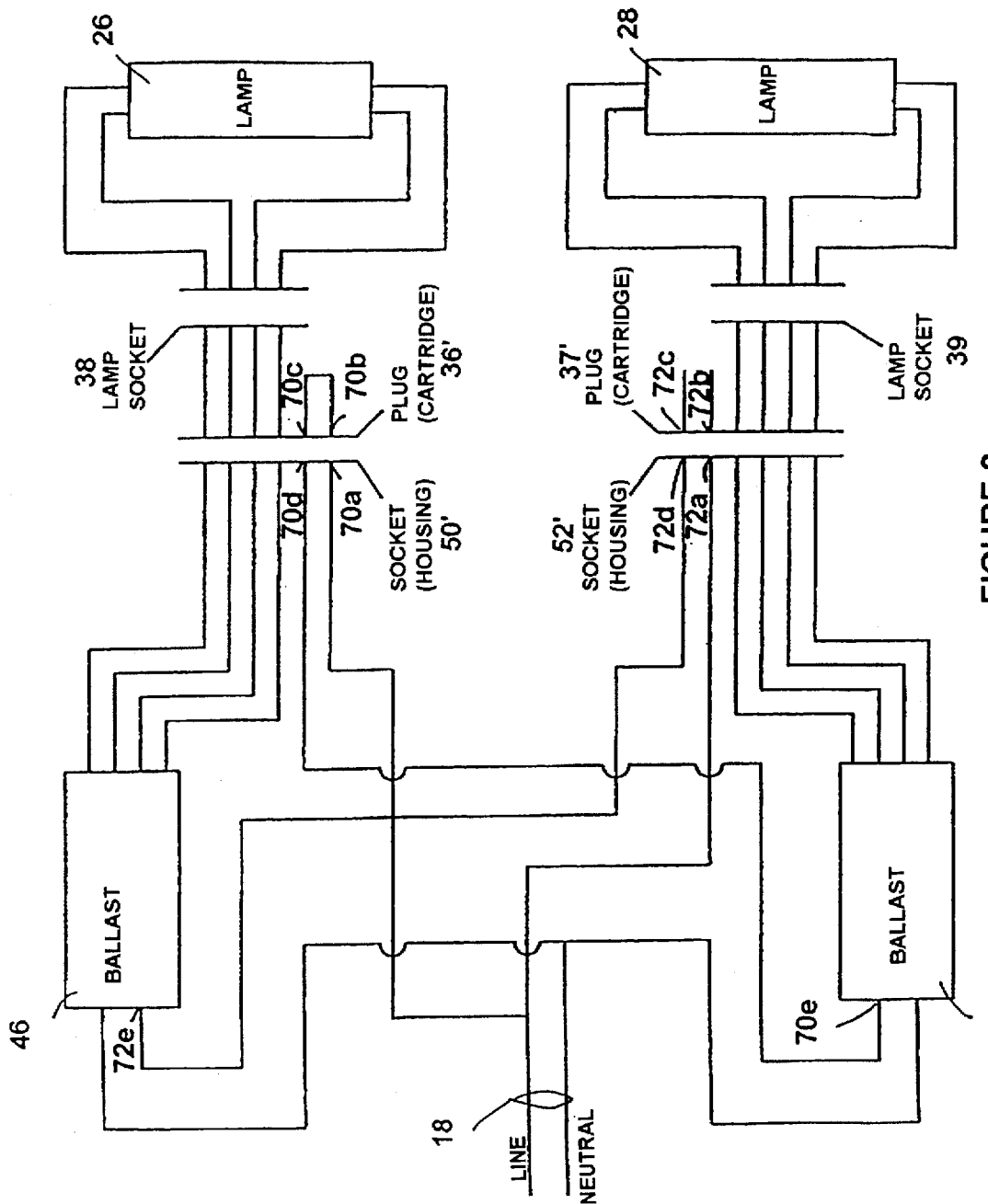
FIG. 8 is a schematic of a dual lamp ultraviolet sterilization unit according to the teachings of FIGS. 6a–7b.

With continued attention to FIG. 5b, mounting plate 34 is configured with apertures sized to receive and hold cartridge plug 36 and lamp socket 38, which is designed to receive the prongs of ultraviolet lamp 26 (28). For ease of explanation, FIG. 5b does not show the required wiring necessary for lamp cartridge 22 (24), including the wiring for cartridge plug 36 and lamp socket 38. However, these wiring connections, as well as the wiring connections necessary for a two lamp ultraviolet sterilization unit 10, are illustrated in FIG. 8 and will be discussed therein. It is to also be noted that while cartridge plug 36 is shown as a four terminal connection, which is sufficient for a single lamp cartridge 22 (24), a six pin cartridge plug is used for the two lamp unit described in FIG. 8.

Lamp cartridge 22 (24) further includes cap 40 within which are held portions of lamp socket 38, cartridge plug 36 and wirings associated therewith. Cap 40 is also configured to include a handle portion 42 and 44 (shown in FIGS. 6a, 6b) allowing for easy gripping of the lamp cartridge 22 (24).

FIG. 6a shows lamp cartridges 22 and 24 inserted within main housing 30. FIG. 6b is an exploded front view of main housing 30 and associated lamp cartridges 22, 24, where housing 30 includes ballasts 46 and 48, each associated with one of respective lamp cartridges 22 and 24. Cartridge sockets 50 and 52 are provided for interconnection with cartridge plugs 36 and 37 (shown in FIG. 7b).

Housing cover 53 includes apertures 54 and 56 into which light pipes 58 and 60 are inserted. A housing plate 62 engages with the housing cover 53 to maintain ballast 46 and 48, as well as cartridge sockets 50, 52 and light pipes 58 and 60 internal of housing cover 53 and housing plate 62. Light pipes 56 and 58 are used to allow a user to observe whether energized ultraviolet lamps within a system are functioning, as the light pipes 58, 60 become illuminated when in contact with ultraviolet rays in the short wave lengths. Housing cover 53 also includes apertures 55a, 55b which are sized to securely receive cap 40.

It is noted that the wiring for ballast 46 and 48 in the present embodiment are more particularly illustrated in FIG. 8. The wirings are not included in these figures to ease the understanding of the construction of ultraviolet sterilization unit 10.

To further explain the present invention, a back side view of main housing 30 is provided in FIG. 7a, with an exploded view of FIG. 7a shown in FIG. 7b. FIG. 7b more clearly sets out that cartridge sockets 50 and 52 are placed within apertures of housing cover 53 such that they are capable of engaging lamp sockets 36 and 37 of lamp cartridges 22 and 24.

It is to be noted that lamp cartridges 22 and 24 are constructed such that ultraviolet lamps 26 and 28 are in an offset relationship with each other. In particular, they are not located within the same plane. This configuration is provided so as to provide a broader coverage of sterilization within the air ducts. However, a sterilization unit without the offsetting can also be constructed according to the teachings of the present invention.

When lamp cartridges 22 and 24 are inserted into main housing 30, lamp holders 32 and 33 are engaged by lamp holder recepticles 32' and 33'. This arrangement increases the stability of the inserted lamps 26 and 28. Also, when lamp cartridges 22 and 24 are inserted into main housing 30, cartridge sockets 50 and 52 are respectively aligned and engaged with cartridge plugs 36 and 37.

As will be further discussed in connection with FIG. 8, the connections of cartridge plugs 36 and 37 with cartridge sockets 50 and 52 energize ultraviolet lamps 26 and 28. Thus, when in an engaged position such as shown in FIGS. 6a and 7a, ultraviolet lamps 26 and 28 are energized and, therefore, actively sterilizing circulating air.

Lamp cartridge 22 (24) can be removed from main housing 30 by applying removal force to handle 42 (44). This action disengages lamp holder 32 (33) from lamp holder connector 32' (33'), as well as disconnects cartridge socket 50 (52) from cartridge plug 36 (37). By breaking the connection between the cartridge socket and cartridge plug, the ultraviolet lamp 26 (28) is de-energized. Thus, the lamps are de-energized and no ultraviolet rays are radiated to a user viewing the ultraviolet lamps 26 and 28. In this manner, a user is automatically protected from harmful ultraviolet rays.

Lamp cartridges 22, 24 will be removed from main housing 30 to either replace ultraviolet lamps 26, 28 within the respective cartridge or to clean lamps 26, 28 to allow them to maintain maximum output. The frequency of cleaning will vary with the condition surrounding the particular installation, however, it is recommended that the cleaning cycle should, under no condition, exceed six months.

To remove lamps 26 and/or 28 from cartridge holders 22 and/or 24 a user can push, twist and pull to unlock and remove the lamps from lamp cartridges 22, 24.

It is to be appreciated, and as illustrated in FIG. 3a, that main housing 30 is attached to cool air return 12 or other appropriate location on the forced air heating and cooling system A. The attachment is made through screw holes 64a, 64b, 64c or by other appropriate attachment, for example by an adhesive arrangement, etc. A benefit obtained by the construction of main housing 30 is the minimal intrusion on the integrity of the cool air return 12 caused by attachment. The use of screws or other attaching devices, through holes 64a–64c and lamp passage openings 66a–66b allow for housing unit 30 to be permanently attached to cool air return 12 with minor cutting of the sheet metal, thereby facilitating easy installation. As previously discussed, lamp cartridges 22 and 24 may be inserted into and removed from housing 30 simply by pulling or pushing handles 42 or 44. Therefore, no tools are needed to remove or insert lamp cartridges 22, 24.

Ballasts 46 and 48 are of a type appropriate for use with ultraviolet germicidal lamps.

FIG. 8 depicts the wiring layout of ultraviolet sterilization unit 10 of the present invention. In this embodiment, the sterilization unit includes two lamps and is constructed such that when one lamp is removed from housing 30 both lamps are de-energized. Through this configuration, no ultraviolet light is emitted from the opening of the removed lamp cartridge 22, 24. One manner in which to obtain the above results is to interconnect lamp cartridges 22, 24 in series with each other. This is accomplished by having power supplied by line 18 to cartridge sockets 50, 52 in turn supply the oppositely corresponding ballast 46 and 48.

In particular, line 70a is shown as being supplied to a pin of a six pin recepticle cartridge socket 50'. When six pin plug cartridge 36' is engaged with cartridge socket 50', a connection is made from line 70a through line 70b, 70c and 70d whereby line 70d is input 70e to ballast 48. Similarly, power is supplied to six pin recepticle cartridge socket 52' at line 72a. When then connected to six pin plug cartridge 37' a circuit is provided to line 72b, 72c and to 72d which in turn supplies ballast 46 at input 72e. Through this arrangement, when either of the cartridge plug/cartridge socket combinations, (i.e. 36' and 50' or 37' and 52') are disconnected thereby de-energizing an associated lamp (26 or 28), the other lamp (26, 28) is also de-energized.

The remaining four pin recepticles of cartridge sockets 50' and 52' connect to the corresponding pins of cartridge plugs 36' and 37', providing a path from ballasts 46, 48 to cartridge plugs 36' and 37'. Cartridge plugs 36' and 37' are in turn wired to lamp sockets 38 and 39. Thus, when lamp sockets 38 and 39 receive the prongs of associated ultraviolet lamps 26 and 28 a complete electrical path is provided for energizing ultraviolet lamps 26 and 28.

Figure 9:
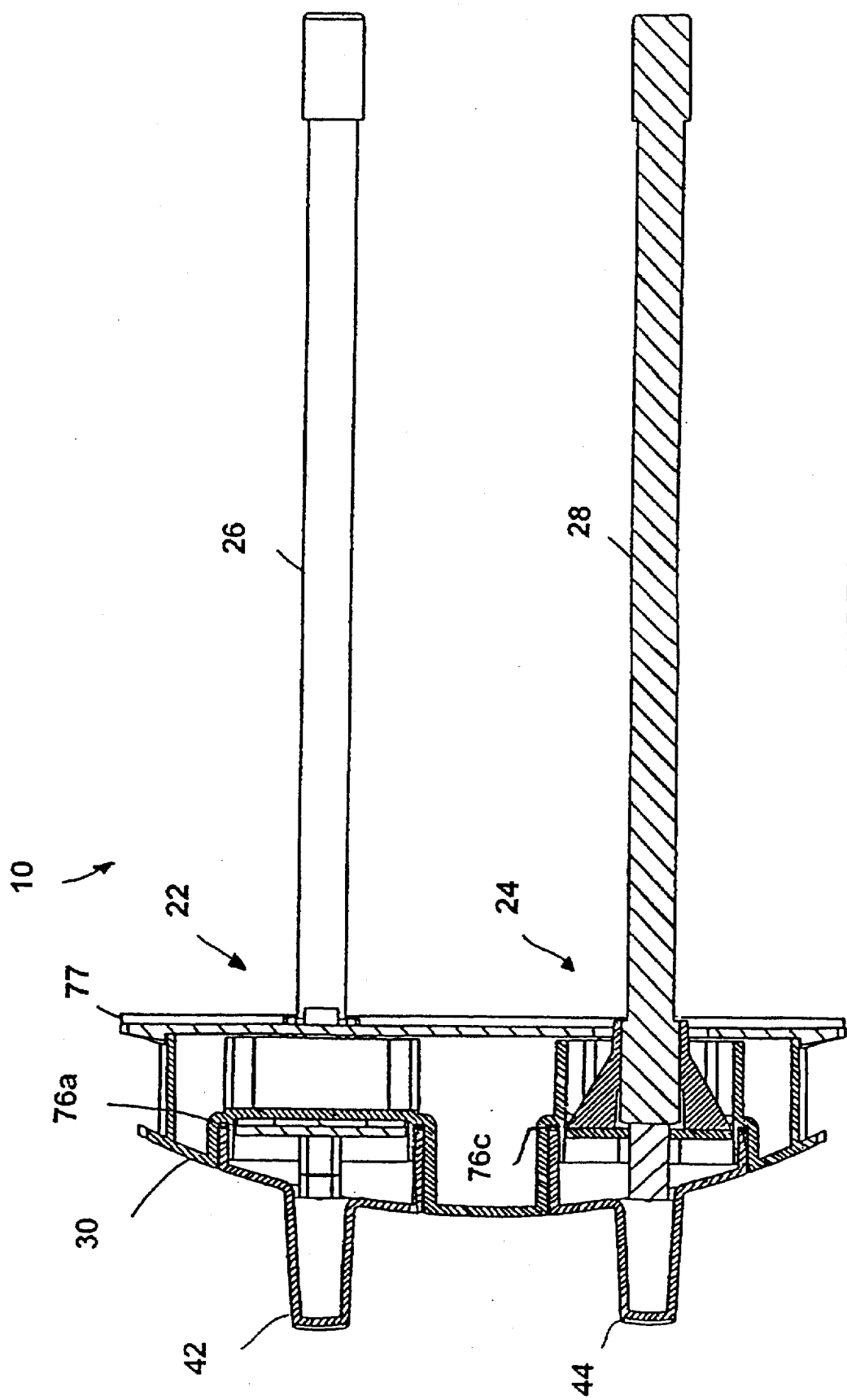
FIG. 9 is a cross-sectional view of the ultraviolet sterilization unit shown in FIGS. 6a–7b; and, FIG. 10 illustrates a lamp cartridge for a two ended ultraviolet lamp.

FIG. 9 is a cross-sectional view of ultraviolet sterilizer unit 10, where lamp cartridges 22 and 24 are inserted within main housing 30. Taking a cross-section view of ultraviolet sterilizer unit 10 results in ultraviolet lamp 28 being shown in cross-section while ultraviolet lamp 26 is shown whole. This view emphasizes the previously discussed offset of lamps 26, 28.

FIG. 9 also illustrates that when lamp cartridges 22 and 24 are inserted into housing 30, locking interconnections ensure there is no direct path for light to pass out of the rear of housing 30. Light from lamps 26 and 28 is blocked from exiting through housing 30 on the cartridge insertion side of the housing by including bends and angles to block light. A further feature of housing 30 are gaskets 76a, 76b and housing gasket 77 used to ensure air from system A does not leak out of sterilization unit 10. Specifically, housing gasket 77 is placed between the wall of system A where openings have been made for insertion of lamps 26, 28 and the face of housing 30 acting as a seal. Gasket rings 76a, 76b are also used to ensure air does not exit through the interface between lamp cartridges 22, 24 and housing 30.

Figure 10:
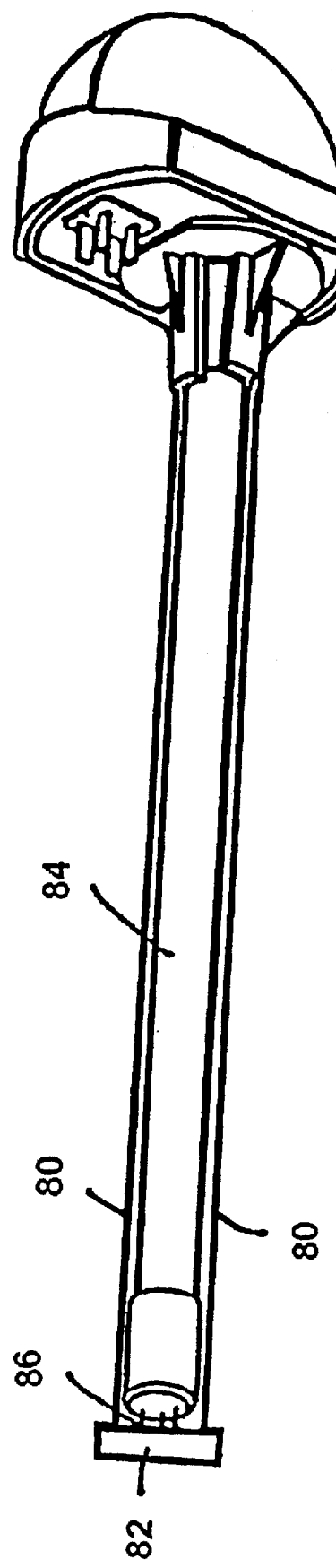

While in the first embodiment ultraviolet lamps 26 and 28 were single ended lamps wherein internal conductive material provide the conduction path from one end of the lamp to another, thereby creating a circuit, two ended lamps may also be used as shown in FIG. 10. In this embodiment, external wires 80 and connector 82 are provided to the far end of the lamp 84 to connect to prongs 86 thereby providing a complete circuit. Such an arrangement may require slightly larger openings in the duct work. However, the external wires and connectors can still be arranged to be carried as part of the lamp cartridge, so that when the lamp cartridge is removed, the external wires and connectors at the far end of the lamp are at the same time removed.

It is noted ultraviolet sterilization unit 10 is shown in FIG. 3a and 3b as being substantially in a horizontal relationship to the cool air return duct 12, particularly, handles 42 and 44 are perpendicular to the bottom of cool air return 12. However, sterilization unit 10 may be inserted in any angled position, i.e. housing 30 may be rotated 90° from what is shown in FIG. 3a. This capability is desirable to ensure that as much of a cross-sectional area of the air heating and cooling system is covered by the ultraviolet lamps 26, 28 as possible. Specifically, it is desirable to have the lamps located at substantially right angles to air flow so that air in the full height of the duct is irradiated, and rotation of unit 10 provides this ability.

While the above invention has been described in detail in connection with a two lamp unit, it is to be appreciated that the present teachings may be extended into multi-lamp units to provide a higher degree of sterilization.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. An ultraviolet sterilization unit comprising:
   a lamp cartridge configured to hold an ultraviolet lamp, and a first portion of an electric circuit for energizing the ultraviolet lamp; and
   a housing including an aperture into which at least a portion of the lamp cartridge is inserted, and a second portion of an electric circuit for energizing the ultraviolet lamp, the second portion configured to connect to the first portion when the lamp cartridge is inserted into the aperture,
   wherein the ultraviolet lamp is only energized when the lamp cartridge is inserted in the housing.

2. The ultraviolet sterilization unit according to claim 1 wherein the housing is configured to accept a plurality of lamp cartridges.

3. The ultraviolet sterilization unit according to claim 2 wherein the second portion includes a ballast and cartridge socket for each lamp cartridge, and the second portion is configured such that removal of any lamp cartridge from the housing de-energizes all the lamps carried by the lamp cartridges.

4. The ultraviolet sterilization unit according to claim 3 wherein the lamps inserted in the housing are offset from each other, thereby increasing the area of effective irradiation.

5. The ultraviolet sterilization unit according to claim 1 wherein the ultraviolet lamp operates in a wavelength range of 253.7 nm, which is optimal for destroying air borne micro-organisms.

6. The ultraviolet sterilization unit according to claim 1 wherein the ultraviolet lamp is a single end lamp.

7. The ultraviolet sterilization unit according to claim 1 wherein the ultraviolet lamp is a double end lamp, and the lamp cartridge includes an external connector and external wires to complete an electric path for the double end lamp.

8. The ultraviolet sterilization unit according to claim 1 wherein the housing is configured to be attached to a section of an air heating and cooling system.

9. The ultraviolet sterilization unit according to claim 8 wherein the housing is capable of being attached to the section of the air heating and cooling system at a plurality of angles.

10. The ultraviolet sterilization unit according to claim 1 wherein the lamp cartridge further includes a handle portion for gripping by a user.

11. The ultraviolet sterilization unit according to claim 1 wherein the housing further includes a lamp indicator which allows an external indication of the status of an energized lamp.

12. The ultraviolet sterilization unit according to claim 1 wherein the first portion of the electric circuit of the lamp cartridge further includes, i) a lamp holder for holding one end of the ultraviolet lamp, ii) a lamp socket which connects to prongs of the ultraviolet lamp, iii) a cartridge plug configured to connect to the second portion carried by the housing, iv) a mounting plate including apertures for holding the plug cartridge and the lamp socket and v) a cap including a handle portion for gripping the lamp cartridge.

13. The ultraviolet sterilization unit according to claim 1 wherein the second portion of the electric circuit of the housing includes, i) a ballast powered by an external power source, ii) a cartridge socket electrically connected to the ballast and further configured to connect to the first portion carried by the lamp cartridge.

14. The ultraviolet sterilization unit according to claim 1 wherein the unit is powered by a 110 VAC.

15. A method of irradiating air borne micro-organisms in an air heating and cooling system comprising:

cutting at least one opening in a section of the air heating and cooling system, in accordance with a predetermined pattern;

attaching a housing to the section of the air heating and cooling system which has been cut according to the predetermined pattern, the housing including an aperture aligned with the at least one opening in the air heating and cooling system, and further including a first portion of an electric circuit; and inserting a lamp cartridge having an ultraviolet lamp connected to a second portion of an electric circuit, into the housing aperture until the first portion and second portion are electrically connected, wherein the ultraviolet lamp is energized when the first and second portions are in electrical connection.

16. The method according to claim 15 further including applying removal-force causing the first portion and the second portion to become disconnected.

17. The method according to claim 15 further including providing a housing gasket to the cut section of the air heating and cooling system, such that the housing gasket is between the cut section and the housing, to stop air leakage.

18. The method according to claim 15 further including providing the housing with a plurality of apertures to accept a plurality of lamp cartridges.

19. The method according to claim 18 further including the step of de-energizing all inserted lamp cartridges when one lamp cartridge is removed.

20. The method according to claim 18 wherein a lamp cartridge is energized only after the ultraviolet lamp has been sufficiently inserted into the air heating and cooling system such that no ultraviolet rays will be emitted externally of the system.

* * * * *